(12) United States Patent
Foxall et al.

(10) Patent No.: US 6,218,125 B1
(45) Date of Patent: Apr. 17, 2001

(54) **ASSAY FOR *CHLAMYDIA TRACHOMATIS* BY AMPLIFICATION AND DETECTION OF *CHLAMYDIA TRACHOMATIS* CRYPTIC PLASMID**

(75) Inventors: Paul A. Foxall, San Mateo, CA (US); Dolores M. Berger, Baltimore, MD (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 09/481,810

(22) Filed: Jan. 12, 2000

Related U.S. Application Data

(62) Division of application No. 08/963,927, filed on Nov. 4, 1997, now Pat. No. 6,096,501.

(51) Int. Cl.[7] .............. C12Q 1/68; C12P 19/34; C07H 21/04
(52) U.S. Cl. ............ 435/6; 435/91.1; 536/24.33
(58) Field of Search ............ 435/6, 91.1; 536/24.33

(56) References Cited

FOREIGN PATENT DOCUMENTS

| | | |
|---|---|---|
| 0 336 412 A2 | 4/1989 | (EP) . |
| 0 420 260 A2 | 9/1990 | (EP) . |
| 0 630 971 A2 | 6/1994 | (EP) . |
| 0 684 315 A1 | 3/1995 | (EP) . |
| 0 812 921 A2 | 12/1997 | (EP) . |
| 93/13221 | 7/1993 | (WO) . |
| WO 95/06756 | 3/1995 | (WO) . |

OTHER PUBLICATIONS

Spears, Patricia A. et al., Analytical Biochemistry; 247, pp. 130–137 (1997).
Walker, G.T. et al., Isothermal in vitro amplification of DNA by a restriction enzyme/DNA polymerase system; *PNAS*, 89, pp. 392–396 (1992).
Walker, G.T. et al., Strand Displacement amplification—an isothermal, in vitro DNA amplification technique; *Nucl. Acids Res.*, 20, pp. 1691–1696 (1992).

*Primary Examiner*—Christopher S. F. Low
*Assistant Examiner*—Devesh Srivastava
(74) *Attorney, Agent, or Firm*—David W. Highet

(57) ABSTRACT

A region of the *Chlamydia trachomatis* cryptic plasmid has been identified which is useful for performing amplification assays to determine specifically whether *C. trachomatis* is present in the sample being tested. Oligonucleotides useful for performing thermal Strand Displacement Assay (tSDA) reactions on this gene are disclosed. The disclosed oligonucleotides can be used in an assay which is specific for all strains of *C. trachomatis* and which does not show cross-reactivity with the genomes of other microorganisms or with human DNA.

21 Claims, 9 Drawing Sheets

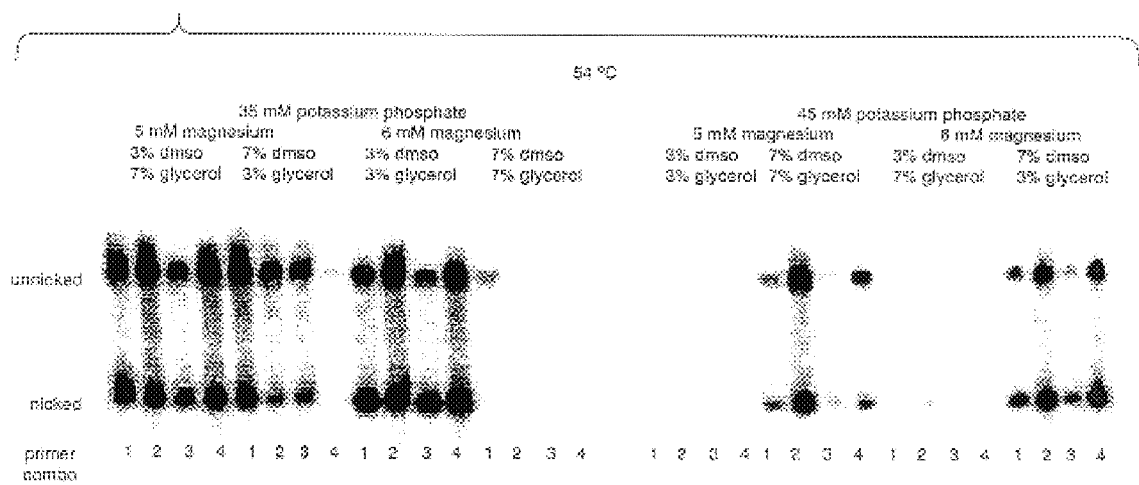

Anti-sense strand detector

Sense strand detector

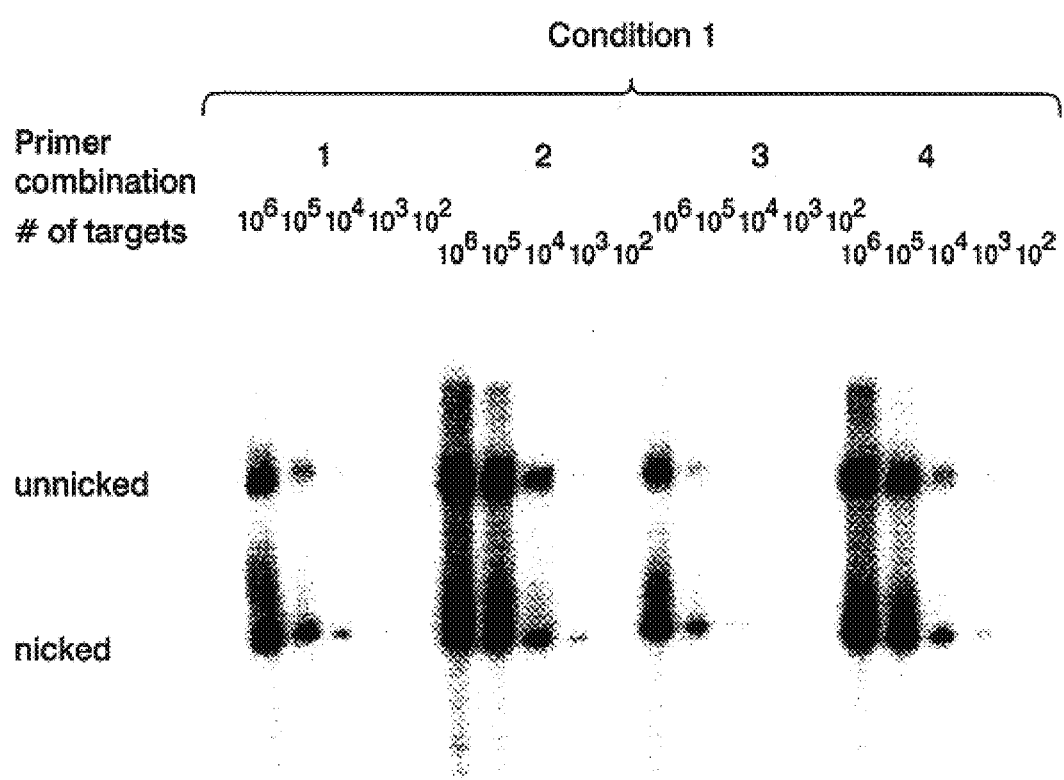

SEQUENCE LISTING (1) GENERAL INFORMATION:

(iii) NUMBER OF SEQUENCES: 30

(2) INFORMATION FOR SEQ ID NO:1:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:1:

GAAGATCGAG TAGACGTAAT AT    22

(2) INFORMATION FOR SEQ ID NO:2:

(i) SEQUENCE CHARACTERISTICS:
      (A) LENGTH: 23 base pairs
      (B) TYPE: nucleic acid
      (C) STRANDEDNESS: single
      (D) TOPOLOGY: linear (xi) SEQUENCE DESCRIPTION: SEQ ID NO:2:

ATAGCAGATA TATCTAGAAC CTT    23

(2) INFORMATION FOR SEQ ID NO:3:

(i) SEQUENCE CHARACTERISTICS:
      (A) LENGTH: 22 base pairs
      (B) TYPE: nucleic acid
      (C) STRANDEDNESS: single
      (D) TOPOLOGY: linear (xi) SEQUENCE DESCRIPTION: SEQ ID NO:3:

TTGGATCGAA ATGTAATACC GA    22

(2) INFORMATION FOR SEQ ID NO:4:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:4:

ACTTCTGATT TTCAAGGTGG AT                                  22

(2) INFORMATION FOR SEQ ID NO:5:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:5:

CAAAACTGCG TCTTTGCTGA TA                                  22

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

GGGTGTGACT GTGAATTTTC C                                   21

(2) INFORMATION FOR SEQ ID NO:7:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:7:

AGTTGGGCAA ATGACAGAGC                                    20

(2) INFORMATION FOR SEQ ID NO:8:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:8:

TGAATAACCC GTTGCATTGA                                    20

(2) INFORMATION FOR SEQ ID NO:9:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:9:

CGATTCCGCT CCAGACTTCT CGGGCGATTA CTTGCAGTTG                  40

(2) INFORMATION FOR SEQ ID NO:10:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (xi) SEQUENCE DESCRIPTION: SEQ ID NO:10:

```
CGATTCCGCT CCAGACTTCT CGGGGATTAC TTGCAGTTG                                 39
```

(2) INFORMATION FOR SEQ ID NO:11:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:11:

```
GAGTAGACGT AATATT                                                         16
```

(2) INFORMATION FOR SEQ ID NO:12:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:12:

```
ACCGCATCGA ATGCATGTCT CGGGATATCT GCTATTTCAT T                             41
```

(2) INFORMATION FOR SEQ ID NO:13:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:13:

```
ACCGCATCGA ATGCATGTCT CGGGATATCT GCTATTTCAT                               40
```

(2) INFORMATION FOR SEQ ID NO:14:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:14:

```
CTCTTAAGGT TCTAG                                                          15
```

(2) INFORMATION FOR SEQ ID NO:15:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:15:

```
CTCATCGGTT GGAGA                                                          15
```

(2) INFORMATION FOR SEQ ID NO:16:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:16:

TCTCCAACCG ATGAG                                              15

(2) INFORMATION FOR SEQ ID NO:17:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (xi) SEQUENCE DESCRIPTION: SEQ ID NO:17:

TAGCACCCGA GTGCTTTGAC GATTTTCTCC AACCGATGAG TTGAT                45

(2) INFORMATION FOR SEQ ID NO:18:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:18:

CAGCAAATAA TCCTTGG                                            17

(2) INFORMATION FOR SEQ ID NO:19:

(i) SEQUENCE CHARACTERISTICS:
        (A) LENGTH: 19 base pairs
        (B) TYPE: nucleic acid
        (C) STRANDEDNESS: single
        (D) TOPOLOGY: linear (xi) SEQUENCE DESCRIPTION: SEQ ID NO:19:

CATTGGTTGA TGAATTATT                                        19

(2) INFORMATION FOR SEQ ID NO:20:

(i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:20:

CGATTCCGCT CCAGACTTCT CGGGACAAAA TCAACACCTG                     40

(2) INFORMATION FOR SEQ ID NO:21:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:21:

CGATTCCGCT CCAGACTTCT CGGGACAAAA TCAACACCTG T                  41

(2) INFORMATION FOR SEQ ID NO:22:

```
    (i) SEQUENCE CHARACTERISTICS:
        (A) LENGTH: 40 base pairs
        (B) TYPE: nucleic acid
        (C) STRANDEDNESS: single
        (D) TOPOLOGY: linear (xi) SEQUENCE DESCRIPTION: SEQ ID NO:22:

ACCGCATCGA ATGCATGTCT CGGGGAGACT GTTAAAGATA                             40

(2) INFORMATION FOR SEQ ID NO:23:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (xi) SEQUENCE DESCRIPTION: SEQ ID NO:23:

ACCGCATCGA ATGCATGTCT CGGGGAGACT GTTAAAGATA T                           41

(2) INFORMATION FOR SEQ ID NO:24:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (xi) SEQUENCE DESCRIPTION: SEQ ID NO:24:

ACCGCATCGA ATGCATGTCT CGGGGAGACT GTTAAAGATA TT                          42

(2) INFORMATION FOR SEQ ID NO:25:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:25:

GTCGCAGCCA AAATG                                                        15

(2) INFORMATION FOR SEQ ID NO:26:

(i) SEQUENCE CHARACTERISTICS:
        (A) LENGTH: 16 base pairs
        (B) TYPE: nucleic acid
        (C) STRANDEDNESS: single
        (D) TOPOLOGY: linear (xi) SEQUENCE DESCRIPTION: SEQ ID NO:26:

ACAGCTTCTG ATGGAA                                                       16

(2) INFORMATION FOR SEQ ID NO:27:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (xi) SEQUENCE DESCRIPTION: SEQ ID NO:27:

GTCGCAGCCA AAAT                                                         14

(2) INFORMATION FOR SEQ ID NO:28:
```

```
    (i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO:28:

GACAGCTTCT GATGGAA                                                    17

(2) INFORMATION FOR SEQ ID NO:29:

(i) SEQUENCE CHARACTERISTICS:
        (A) LENGTH: 44 base pairs
        (B) TYPE: nucleic acid
        (C) STRANDEDNESS: single
        (D) TOPOLOGY: linear (xi) SEQUENCE DESCRIPTION: SEQ ID NO:29:

TAGCACCCGA GTGCTCGCAG CCAAAATGAC AGCTTCTGAT GGAA                       44

(2) INFORMATION FOR SEQ ID NO:30:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (xi) SEQUENCE DESCRIPTION: SEQ ID NO:30:

TAGCACCCGA GTGCT                                                      15
```

US 6,218,125 B1

ASSAY FOR *CHLAMYDIA TRACHOMATIS* BY AMPLIFICATION AND DETECTION OF *CHLAMYDIA TRACHOMATIS* CRYPTIC PLASMID

This application is a divisional of application 08/963,927, filed Nov. 4, 1997, now U.S. Pat. No. 6,096,501.

FIELD OF THE INVENTION

The present invention relates to methods for determining the presence or absence of *Chlamydia trachomatis* in patients. The method involves using nucleic acid primers to amplify specifically the *Chlamydia trachomatis* cryptic plasmid, preferably using one of the techniques of Strand Displacement Amplification (SDA), thermophilic Strand Displacement Amplification (tSDA) or fluorescent real time thermal Strand Displacement Amplification.

BACKGROUND OF THE INVENTION

*Chlamydia trachomatis* is the causative agent of trachoma (which is the greatest single cause of blindness), inclusion conjunctivitis, infant pneumonitis, urethritis and lymphogranuloma venereum. Diagnosis and detection of this organism is often on the basis of the pathologic or clinical findings and may be confirmed by isolation and staining techniques.

*C. trachomatis* includes a cryptic plasmid which is approximately 7.5 kb in size and is present in multiple copies in the organism. The presence of multiple copies makes this plasmid a good target for diagnostic purposes for assays using nucleic acid amplification techniques.

The following terms are defined herein as follows:

An amplification primer is a primer for amplification of a target sequence by extension of the primer after hybridization to the target sequence. Amplification primers are typically about 10–75 nucleotides in length, preferably about 15–50 nucleotides in length. The total length of an amplification primer for SDA is typically about 25–50 nucleotides. The 3' end of an SDA amplification primer (the target binding sequence) hybridizes at the 5' end of the target sequence. The target binding sequence is about 10–25 nucleotides in length and confers hybridization specificity on the amplification primer. The SDA amplification primer further comprises a recognition site for a restriction endonuclease 5' to the target binding sequence. The recognition site is for a restriction endonuclease which will nick one strand of a DNA duplex when the recognition site is hemimodified, as described by G. Walker, et al. (1992. *PNAS* 89:392–396 and 1992 *Nucl. Acids Res.* 20:1691–1696). The nucleotides 5' to the restriction endonuclease recognition site (the "tail") function as a polymerase repriming site when the remainder of the amplification primer is nicked and displaced during SDA. The repriming function of the tail nucleotides sustains the SDA reaction and allows synthesis of multiple amplicons from a single target molecule. The tail is typically about 10–25 nucleotides in length. Its length and sequence are generally not critical and can be routinely selected and modified. As the target binding sequence is the portion of a primer which determines its target-specificity, for amplification methods which do not require specialized sequences at the ends of the target the amplification primer generally consists essentially of only the target binding sequence. For amplification methods which require specialized sequences appended to the target other than the nickable restriction endonuclease recognition site and the tail of SDA (e.g., an RNA polymerase promoter for 3SR, NASBA or transcription based amplification), the required specialized sequence may be linked to the target binding sequence using routine methods for preparation of oligonucleotides without altering the hybridization specificity of the primer.

A bumper primer or external primer is a primer used to displace primer extension products in isothermal amplification reactions. The bumper primer anneals to a target sequence upstream of the amplification primer such that extension of the bumper primer displaces the downstream amplification primer and its extension product.

The terms target or target sequence refer to nucleic acid sequences to be amplified. These include the original nucleic acid sequence to be amplified, the complementary second strand of the original nucleic acid sequence to be amplified and either strand of a copy of the original sequence which is produced by the amplification reaction. These copies serve as amplifiable targets by virtue of the fact that they contain copies of the sequence to which the amplification primers hybridize.

Copies of the target sequence which are generated during the amplification reaction are referred to as amplification products, amplimers or amplicons.

The term extension product refers to the copy of a target sequence produced by hybridization of a primer and extension of the primer by polymerase using the target sequence as a template.

The term species-specific refers to detection, amplification or oligonucleotide hybridization in a species of organism or a group of related species without substantial detection, amplification or oligonucleotide hybridization in other species of the same genus or species of a different genus.

The term assay probe refers to any oligonucleotide used to facilitate detection or identification of a nucleic acid. For example, in the present invention, assay probes are used for detection or identification of *C. trachomatis* cryptic plasmid nucleic acids. Detector probes, detector primers, capture probes and signal primers as described below are examples of assay probes.

SUMMARY OF THE INVENTION

The present invention provides oligonucleotides useful as amplification primers and assay probes for specific detection and identification of *Chlamydia trachomatis*. The specific probes amplify the *C. trachomatis* cryptic plasmid with little or no detectable amplification of either human DNA or DNA of other microorganisms. Two regions of the *C. trachomatis* cryptic plasmid were selected to develop nucleic acid primers which would specifically amplify this plasmid without showing crossreactivity with human DNA or other microorganism DNA.

The oligonucleotides of the invention may be used after culture as a means for confirming the identity of the cultured organism. Alternatively, they may be used prior to culture or in place of culture for detection and identification of *C. trachomatis* cryptic plasmid nucleic acid using known amplification methods. In either case, the inventive oligonucleotides and assay methods provide a means for rapidly discriminating between *C. trachomatis* and other microorganisms, allowing the practitioner to identify rapidly this microorganism without resorting to the more traditional procedures customarily relied upon. Such rapid identification of the specific etiological agent involved in an infection provides information which can be used to determine appropriate therapy within a short period of time.

BRIEF DESCRIPTION OF THE DRAWINGS

The various objects, advantages and novel features of the present invention will be readily understood from the following detailed description when read in conjunction with the appended drawings in which:

FIGS. 2A–B show the phosphorimages resulting from using a matrix of test conditions using various combinations of primers, buffer conditions and temperatures to perform tSDA with a portion of C. trachomatis cryptic plasmid (in plasmid pCT 16) as the target.

DETAILED DESCRIPTION OF THE INVENTION

Figure 1:
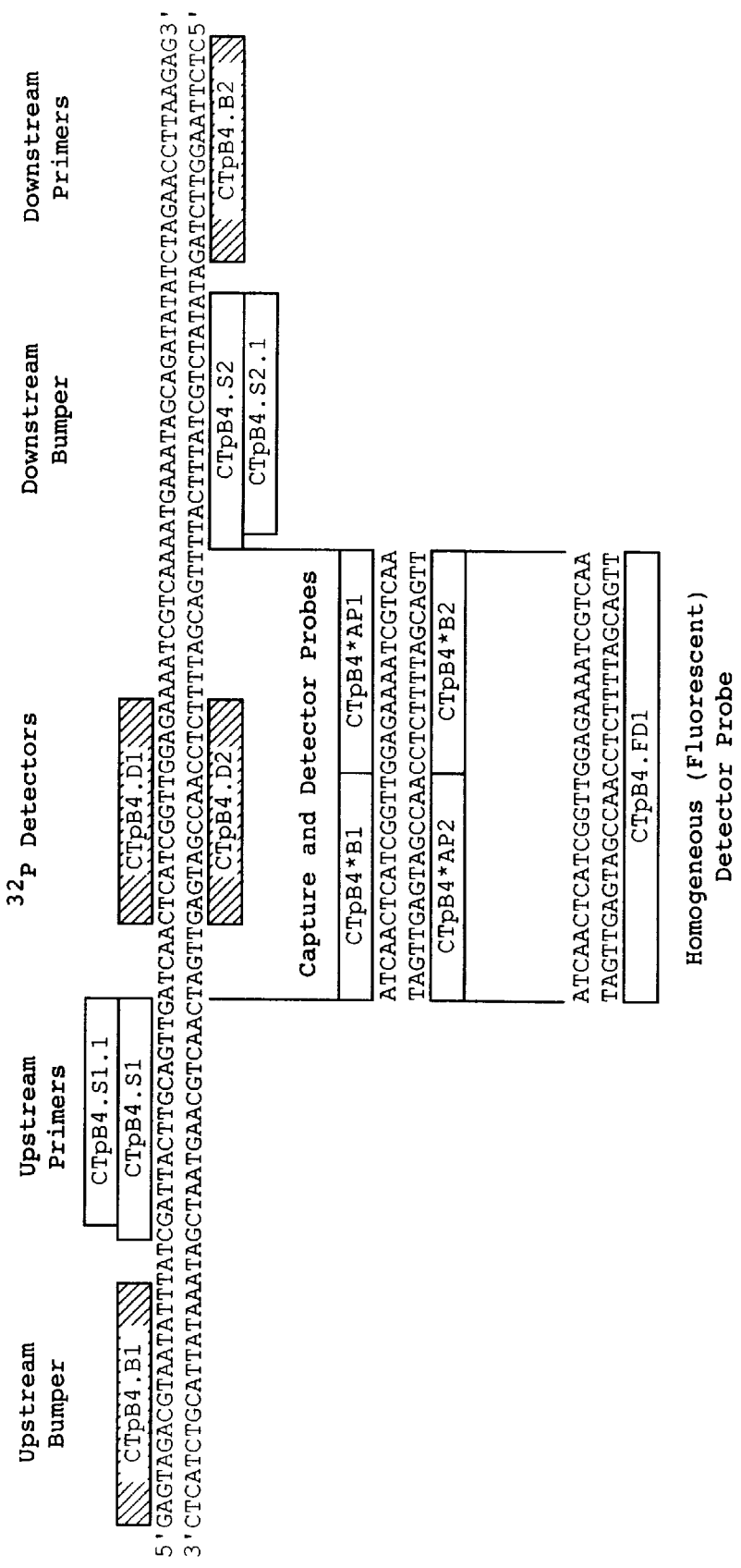
FIG. 1 indicates bumpers, primers and detectors used for System B.
Figure 2A:
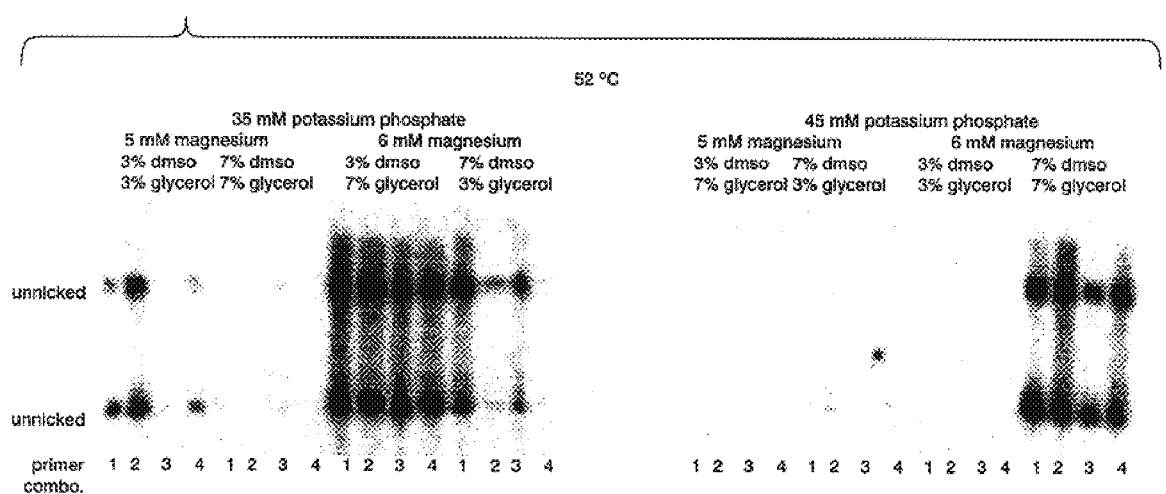

The present invention relates to oligonucleotides, amplification primers and assay probes which exhibit Chlamydia trachomatis-specificity in nucleic acid amplification reactions. Also provided are methods for detecting and identifying C. trachomatis cryptic plasmid nucleic acids using the oligonucleotides of the invention. The preferred methods are to use SDA, tSDA or homogeneous real time fluorescent tSDA. These methods are known to those skilled in the art from references such as U.S. Pat. No. 5,547,861 and U.S. Pat. No. 5,648,211, U.S. patent application Ser. No. 08/865, 675, filed May 30, 1997 and U.S. patent application Ser. No. 08/855,085 filed May 13, 1997, the disclosures of which are hereby specifically incorporated herein by reference.

The primers of the present invention were designed based on the sequence of C. trachomatis cryptic plasmid which is available from GenBank. The plasmid sequences were aligned and sectioned into manageable regions (300–500 bp). Two regions (B and F) were selected for further study. Regions B and F were sequenced for several serovars of C. trachomatis and tSDA systems were designed in these areas. The primers used to amplify and sequence the B and F regions, respectively, are:

B Region Amplification and Sequencing Primers

CTpB1P 5'-GAAGATCGAGTAGACGTAATAT-3' (SEQ ID NO: 1)

CTpB2P 5' ATAGCAGATATATCTAGAACCTT-3' (SEQ ID NO: 2)

CTpB3N 5'-TTGGATCGAAATGTAATACCGA-3' (SEQ ID NO: 3)

CTpB4N 5'-ACTTCTGATTTTCAAGGTGGAT-3' (SEQ ID NO: 4)

F Region Amplification and Sequencing Primers

CTpFPL 5'-CAAAACTGCGTCTTTGCTGATA-3' (SEQ ID NO: 5)

CTpFPR 5'-GGGTGTGACTGTGAATTTTCC-3' (SEQ ID NO: 6)

CTpFSL 5'-AGTTGGGCAAATGACAGAGC-3' (SEQ ID NO: 7)

CTpFSR 5'-TGAATAACCCGTTGCATTGA-3' (SEQ ID NO: 8)

Systems of detection relating to analysis of regions B and F are described below. Various combinations of primers were tested for specificity and sensitivity in tSDA reactions and in fluorescent real time tSDA reactions.

As nucleic acids do not require complete complementarity in order to hybridize, it is to be understood that the probe and primer sequences herein disclosed may be modified to some extent without loss of utility as C. trachomatis-specific probes and primers. As is known in the art, hybridization of complementary and partially complementary nucleic acid sequences may be obtained by adjustment of the hybridization conditions to increase or decrease stringency (i.e., adjustment of hybridization temperature or salt content of the buffer). Such minor modifications of the disclosed sequences and any necessary adjustments of hybridization conditions to maintain C. trachomatis-specificity require only routine experimentation and are within the ordinary skill in the art.

The amplification products generated using the inventive primers may be detected by a characteristic size, for example on polyacrylamide or agarose gels stained with ethidium bromide. Alternatively, amplified C. trachomatis cryptic plasmid target sequences may be detected by means of an assay probe, which is an oligonucleotide tagged with a detectable label. In one embodiment, at least one tagged assay probe may be used for detection of amplified target sequences by hybridization (a detector probe), by hybridization and extension as described by Walker, et al., Nucl. Acids Res., supra (a detector primer) or by hybridization, extension and conversion to double stranded form as described in EP 0 678 582 (a signal primer). Preferably, the assay probe is selected to hybridize to a sequence in the target which is between the amplification primers, i.e., it should be an internal assay probe. Alternatively, an amplification primer or the target binding sequence thereof may be used as the assay probe.

The detectable label of the assay probe is a moiety which can be detected either directly or indirectly as an indication of the presence of the target nucleic acid. For direct detection of the label, assay probes may be tagged with a radioisotope and detected by autoradiography or tagged with a fluorescent moiety and detected by fluorescence as is known in the art. Alternatively, the assay probes may be indirectly detected by tagging with a label which requires additional reagents to render it detectable. Indirectly detectable labels include, for example, chemiluminescent agents, enzymes which produce visible reaction products and ligands (e.g., haptens, antibodies or antigens) which may be detected by binding to labeled specific binding partners (e.g., antibodies or antigens/haptens). Ligands are also useful immobilizing the ligand-labeled oligonucleotide (the capture probe) on a solid phase to facilitate its detection. Particularly useful labels include biotin (detectable by binding to labeled avidin or streptavidin) and enzymes such as horseradish peroxidase or alkaline phosphatase (detectable by addition of enzyme substrates to produce colored reaction products). Methods for adding such labels to, or including such labels in, oligonucleotides are well known in the art and any of these methods are suitable for use in the present invention.

Examples of specific detection methods which may be employed include a chemiluminescent method in which amplified products are detected using a biotinylated capture probe and an enzyme-conjugated detector probe as described in U.S. Pat. No. 5,470,723. After hybridization of these two assay probes to different sites in the assay region of the target sequence (between the binding sites of the two amplification primers), the complex is captured on a streptavidin-coated microtiter plate by means of the capture probe, and the chemiluminescent signal is developed and read in a luminometer. As another alternative for detection of amplification products, a signal primer as described in EP 0 678 582 may be included in the SDA reaction. In this embodiment, labeled secondary amplification products are generated during SDA in a target amplification-dependent manner and may be detected as an indication of target amplification by means of the associated label.

For commercial convenience, amplification primers for specific detection and identification of *C. trachomatis* cryptic plasmid nucleic acids may be packaged in the form of a kit. Typically, such a kit contains at least one pair of amplification primers according to the present invention. Reagents for performing a nucleic acid amplification reaction may also be included with the *C. trachomatis* cryptic plasmid-specific amplification primers, for example, buffers, additional primers, nucleotide triphosphates, enzymes, etc. The components of the kit are packaged together in a common container, optionally including instructions for performing a specific embodiment of the inventive methods. Other optional components may also be included in the kit, e.g., an oligonucleotide tagged with a label suitable for use as an assay probe, and/or reagents or means for detecting the label.

The target binding sequences of the amplification primers confer species hybridization specificity on the oligonucleotides and therefore provide species-specificity to the amplification reaction. Other sequences, as required for performance of a selected amplification reaction, may optionally be added to the target binding sequences disclosed herein without altering the species-specificity of the oligonucleotide. By way of example, the *C. trachomatis* cryptic plasmid-specific amplification primers of the invention may contain a recognition site for the restriction endonuclease BsoBI which is nicked during the SDA reaction. It will be apparent to one skilled in the art that other nickable restriction endonuclease recognition sites may be substituted for the BsoBI recognition site, including but not limited to those recognition sites disclosed in EP 0 684 315. Preferably, the recognition site is for a thermophilic restriction endonuclease so that the amplification reaction may be performed under the conditions of thermophilic SDA (tSDA). Similarly, the tail sequence of the amplification primer (5' to the restriction endonuclease recognition site) is generally not critical, although the restriction site used for SDA and sequences which will hybridize either to their own target binding sequence or to the other primers should be avoided. Some amplification primers for SDA according to the invention therefore consist of 3' target binding sequences, a nickable restriction endonuclease recognition site 5' to the target binding sequence and a tail sequence about 10–25 nucleotides in length 5' to the restriction endonuclease recognition site. The nickable restriction endonuclease recognition site and the tail sequence are sequences required for the SDA reaction. For other amplification reactions, the amplification primers according to the invention may consist of the disclosed target binding sequences only (e.g., for PCR) or the target binding sequence and additional sequences required for the selected amplification reaction (e.g., sequences required for SDA as described above or a promoter recognized by RNA polymerase for 3SR).

In SDA, the bumper primers are not essential for species-specificity, as they function to displace the downstream, species-specific amplification primers. It is only required that the bumper primers hybridize to the target upstream from the amplification primers so that when they are extended they will displace the amplification primer and its extension product. The particular sequence of the bumper primer is therefore generally not critical, and may be derived from any upstream target sequence which is sufficiently close to the binding site of the amplification primer to allow displacement of the amplification primer extension product upon extension of the bumper primer. Occasional mismatches with the target in the bumper primer sequence or some cross-hybridization with non-target sequences do not generally negatively affect amplification efficiency as long as the bumper primer remains capable of hybridizing to the specific target sequence. However, the bumper primers described herein are species-specific for *C. trachomatis* and may therefore also be used as target binding sequences in amplification primers, if desired.

Amplification reactions employing the primers of the invention may incorporate thymine as taught by Walker, et al., supra, or they may wholly or partially substitute 2'-deoxyuridine 5'-triphosphate for TTP in the reaction to reduce cross-contamination of subsequent amplification reactions, e.g., as taught in EP 0 624 643. dU (uridine) is incorporated into amplification products and can be excised by treatment with uracil DNA glycosylase (UDG). These abasic sites render the amplification product unamplifiable in subsequent amplification reactions. UDG may be inactivated by uracil DNA glycosylase inhibitor (Ugi) prior to performing the subsequent amplification to prevent excision of dU in newly-formed amplification products.

Other systems were developed for performing tSDA using different combinations of primers, bumpers and detectors. However, these other systems were not preferred for various reasons such as lack of adequate specificity, narrow range of optimal conditions and lack of robustness.

FIG. 1 indicates the primers, bumpers and detectors for system B. This system is discussed in the Examples. System B is located at the 5' end of region B. In the initial experiments two upstream primers and two downstream primers were designed along with one upstream bumper and one downstream bumper. These were used in various combinations along with detectors. The primers, bumpers and detectors used in system B are shown below. The hybridization region of the primers is underlined and the BsoBI restriction site is italicized.

Upstream Primers:
CTpB4.S1
5'-CGATTCCGCTCCAGACTTCTCGGGCGATTA CTTGCAGTTG-3' (SEQ ID NO:9)
CTpB4.S1.1
5'-CGATTCCGCTCCAGACTTCTCGGGGATTAC TTGCAGTTG-3' (SEQ ID NO: 10)
Upstream Bumper:
CTpB4.B1 5'-GAGTAGACGTAATATT-3' (SEQ ID NO: 11)
Downstream Primers:
CTpB4.S2
5'-ACCGCATCGAATGCATGTCTCGGGATATCT GCTATTTCATT-3' (SEQ ID NO: 12)
CTpB4.S2.1
5'-ACCGCATCGAATGCATGTCTCGGGATATCT GCTATTTCAT-3' (SEQ ID NO: 13)
Downstream Bumper:
CTpB4.B2 5'-CTCTTAAGGTTCTAG-3' (SEQ ID NO: 14)
$^{32}$P Detectors:
CTpB4.D1 5'-CTCATCGGTTGGAGA-3' (SEQ ID NO: 15)
CTpB4.D2 5'-TCTCCAACCGATGAG-3' (SEQ ID NO: 16)

Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occurs concurrently in the reaction mix. This is in contrast to polymerase chain reaction (PCR), in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'–3' exonuclease deficient polymerase incorporating an α-thio deoxynucleoside triphosphate (α-thio dNTP), 3) nicking of a hemimodified double stranded restriction site, 4) dissociation of the restriction enzyme from the nick site, and 5) extension from the 3' end of the nick by the 5'–3' exonuclease deficient polymerase with displacement of the downstream newly synthesized strand. Nicking, polymer- Fluorescent Detector:

```
CtpB4.FD1    5'-TAGCACCCGAGTGCTTTGACGATTTTCTCCAACCGATGAGTTGAT-3'    (SEQ ID NO: 17)
                |                   |
                FAM                 ROX
```

In initial screening experiments, primer mixes were prepared to contain one upstream primer and one downstream primer. The four possible primer mixes are:
Combination 1
CTpB4.S1 (SEQ ID NO: 9)
CTpB4.S2 (SEQ ID NO: 12)
Combination 2
CTpB4.S1.1 (SEQ ID NO: 10)
CTpB4.S2 (SEQ ID NO: 12)
Combination 3
CTpB4.S1 (SEQ ID NO: 9)
CTpB4.S2.1 (SEQ ID NO: 13)
Combination 4
CTpB4.S1.1 (SEQ ID NO: 10)
CTpB4.S2.1 (SEQ ID NO: 13)

All of the primer mixes also contained the upstream and downstream bumpers. The primers and bumpers are used at a final concentration of 0.5 and 0.05 μM, respectively.

The above primer mixes are used in the study of region B of the Cryptic plasmid and are further discussed in the Examples. Other primers which hybridize to region F of the Cryptic plasmid and which also are useful for assaying for C. trachomatis are also discussed in the Examples. Later Examples also disclose methods of using primers for region F for use in homogeneous real time fluorescent tSDA.

The primers and probes of System B are preferably used in a tSDA real time fluorescence energy transfer method.

ization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. (1992, Nuc. Acids Res., supra) and in U.S. Pat. No. 5,270,184 (hereby incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as targets for binding of the opposite amplification and bumper primer (e.g., the extension product of $S_1$ binds $S_2$ and $B_2$). The next cycle of extension and displacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

To prevent cross-contamination of one SDA reaction by the amplification products of another, dUTP may be incorporated into SDA-amplified DNA in place of dTTP without inhibition of the amplification reaction. The uracil-modified nucleic acids may then be specifically recognized and inactivated by treatment with uracil DNA glycosylase (UDG). Therefore, if dUTP is incorporated into SDA-amplified DNA in a prior reaction, any subsequent SDA reactions can be treated with UDG prior to amplification of double stranded targets, and any dU containing DNA from previously amplified reactions will be rendered unamplifiable. The target DNA to be amplified in the subsequent reaction does not contain dU and will not be affected by the UDG treatment. UDG may then be inhibited by treatment with Ugi prior to amplification of the target. Alternatively, UDG may be heat-inactivated. In thermophilic SDA, the higher temperature of the reaction itself ($\geq 50°$ C.) can be used to concurrently inactivate UDG and amplify the target.

SDA requires a polymerase which lacks 5'-3' exonuclease activity, initiates polymerization at a single stranded nick in double stranded nucleic acids, and displaces the strand downstream of the nick while generating a new complementary strand using the unnicked strand as a template. The polymerase must extend by adding nucleotides to a free 3'-OH. To optimize the SDA reaction, it is also desirable that the polymerase be highly processive to maximize the length of target sequence which can be amplified. Highly processive polymerases are capable of polymerizing new strands of significant length before dissociating and terminating synthesis of the extension product. Displacement activity is essential to the amplification reaction, as it makes the target available for synthesis of additional copies and generates the single stranded extension product to which a second amplification primer may hybridize in exponential amplification reactions. Nicking activity is also of great importance, as it is nicking which perpetuates the reaction and allows subsequent rounds of target amplification to initiate.

Thermophilic SDA is performed essentially as the conventional SDA described by Walker, et al. (1992, *PNAS* and *Nuc. Acids Res.*, supra), with substitution of the desired thermostable polymerase and thermostable restriction endonuclease. Of course, the temperature of the reaction will be adjusted to the higher temperature suitable for the substituted enzymes and the HincII restriction endonuclease recognition/cleavage site will be replaced by the appropriate restriction endonuclease recognition/cleavage site for the selected thermostable endonuclease. Also in contrast to Walker, et al., the practitioner may include the enzymes in the reaction mixture prior to the initial denaturation step if they are sufficiently stable at the denaturation temperature. Preferred restriction endonucleases for use in thermophilic SDA are BsrI, BstNI, BsmAI, BsII and BsoBI (New England BioLabs), and BstOI (Promega). The preferred thermophilic polymerases are Bca (Panvera) and Bst (New England Biolabs).

Homogeneous real time fluorescent tSDA is a modification of tSDA. It employs detector oligonucleotides to produce reduced fluorescence quenching in a target-dependent manner. The detector oligonucleotides contain a donor/acceptor dye pair linked such that fluorescence quenching occurs in the absence of target. Unfolding or linearization of an intramolecularly base-paired secondary structure in the detector oligonucleotide in the presence of the target increases the distance between the dyes and reduces fluorescence quenching. Unfolding of the base-paired secondary structure typically involves intermolecular base-pairing between the sequence of the secondary structure and a complementary strand such that the secondary structure is at least partially disrupted. It may be fully linearized in the presence of a complementary strand of sufficient length. In a preferred embodiment, a restriction endonuclease recognition site (RERS) is present between the two dyes such that intermolecular base-pairing between the secondary structure and a complementary strand also renders the RERS double-stranded and cleavable or nickable by a restriction endonuclease. Cleavage or nicking by the restriction endonuclease separates the donor and acceptor dyes onto separate nucleic acid fragments, further contributing to decreased quenching. In either embodiment, an associated change in a fluorescence parameter (e.g., an increase in donor fluorescence intensity, a decrease in acceptor fluorescence intensity or a ratio of fluorescence before and after unfolding) is monitored as an indication of the presence of the target sequence. Monitoring a change in donor fluorescence intensity is preferred, as this change is typically larger than the change in acceptor fluorescence intensity. Other fluorescence parameters such as a change in fluorescence lifetime may also be monitored.

A detector oligonucleotide for homogeneous real time fluorescent tSDA is an oligonucleotide which comprises a single-stranded 5' or 3' section which hybridizes to the target sequence (the target binding sequence) and an intramolecularly base-paired secondary structure adjacent to the target binding sequence. The detector oligonucleotides of the invention further comprise a donor/acceptor dye pair linked to the detector oligonucleotide such that donor fluorescence is quenched when the secondary structure is intramolecularly base-paired and unfolding or linearization of the secondary structure results in a decrease in fluorescence quenching. Cleavage of an oligonucleotide refers to breaking the phosphodiester bonds of both strands of a DNA duplex or breaking the phosphodiester bond of single-stranded DNA. This is in contrast to nicking, which refers to breaking the phosphodiester bond of only one of the two strands in a DNA duplex.

The detector oligonucleotides of the invention for homogeneous real time fluorescent tSDA comprise a sequence which forms an intramolecularly base-paired secondary structure under the selected reaction conditions for primer extension or hybridization. The secondary structure is positioned adjacent to the target binding sequence of the detector oligonucleotide so that at least a portion of the target binding sequence forms a single-stranded 3' or 5' tail. As used herein, the term "adjacent to the target binding sequence" means that all or part of the target binding sequence is left single-stranded in a 5' or 3' tail which is available for hybridization to the target. That is, the secondary structure does not comprise the entire target binding sequence. A portion of the target binding sequence may be involved in the intramolecular base-pairing in the secondary structure, it may include all or part of a first sequence involved in intramolecular base-pairing in the secondary structure, it may include all or part of a first sequence involved in intramolecular base-pairing in the secondary structure but preferably does not extend into its complementary sequence. For example, if the secondary structure is a stem-loop structure (e.g., a "hairpin") and the target binding sequence of the detector oligonucleotide is present as a single-stranded 3' tail, the target binding sequence may also extend through all or part of the first arm of the stem and, optionally, through all or part of the loop. However, the target binding sequence preferably does not extend into the second arm of the sequence involved in stem intramolecular base-pairing. That is, it is desirable to avoid having both sequences involved in intramolecular base-pairing in a secondary structure capable of hybridizing to the target. Mismatches in the intramolecularly base-paired portion of the detector oligonucleotide secondary structure may reduce the magnitude of the change in fluorescence in the presence of target but are acceptable if assay sensitivity is not a concern. Mismatches in the target binding sequence of the single-stranded tail are also acceptable but may similarly reduce assay sensitivity and/or specificity. However, it is a feature of the present invention that perfect base-pairing in both the secondary structure and the target binding sequence do not compromise the reaction. Perfect matches in the sequences involved in hybridization improve assay specificity without negative effects on reaction kinetics.

When added to the amplification reaction, the detector oligonucleotide signal primers of the invention are converted to double-stranded form by hybridization and extension of an amplification primer as described above. Strand displacement by the polymerase also unfolds or linearizes the secondary structure and converts it to double-stranded from by synthesis of a complementary strand. The RERS, if present, also becomes double-stranded and cleavable or nickable by the restriction endonuclease. As the secondary structure is unfolded or linearized by the strand displacing activity of the polymerase, the distance between the donor and acceptor dye is increased, thereby reducing quenching of donor fluorescence. The associated change in fluorescence of either the donor or acceptor dye may be monitored or detected as an indication of amplification of the target sequence. Cleavage or nicking of the RERS generally further increases the magnitude of the change in fluorescence by producing two separate fragments of the double-stranded secondary amplification product, each having one of the two dyes linked to it. These fragments are free to diffuse in the reaction solution, further increasing the distance between the dyes of the donor/acceptor pair. An increase in donor fluorescence intensity or a decrease in acceptor fluorescence intensity may be detected and/or monitored as an indication that target amplification is occurring or has occurred, but other fluorescence parameters which are affected by the proximity of the donor/acceptor dye pair may also be monitored. A change in fluorescence intensity of the donor or acceptor may also be detected as a change in a ratio of donor and/or acceptor fluorescence intensities. For example, a change in fluorescence intensity may be detected as a) an increase in the ratio of donor fluorophore fluorescence after linearizing or unfolding the secondary structure and donor fluorophore fluorescence in the detector oligonucleotide prior to linearizing or unfolding, or b) as a decrease in the ratio of acceptor dye fluorescence after linearizing or unfolding and acceptor dye fluorescence in the detector oligonucleotide prior to linearizing or unfolding.

It will be apparent that, in addition to SDA, the detector oligonucleotides of the invention may be adapted for use as signal primers in other primer extension amplification methods (e.g., PCR, 3SR, TMA or NASBA). For example, the methods may be adapted for use in PCR by using PCR amplification primers and a strand displacing DNA polymerase which lacks 5'→3' exonuclease activity (e.g., Sequencing Grade Taq from Promega or exo$^-$ Vent or exo$^-$ Deep Vent from New England BioLabs) in the PCR. The detector oligonucleotide signal primers hybridize to the target downstream from the PCR amplification primers, are displaced and are rendered double-stranded essentially as described for SDA. In PCR any RERS may optionally be selected for use in the detector oligonucleotide, as there are typically no modified deoxynucleoside triphosphates present which might induce nicking rather than cleavage of the RERS. As thermocycling is a feature of amplification by PCR, the restriction endonuclease is preferably added at low temperature after the final cycle of primer annealing and extension for end-point detection of amplification. However, a thermophilic restriction endonuclease which remains active through the high temperature phases of the PCR reaction could be present during amplification to provide a real-time assay. As in SDA systems, linearization of the secondary structure and separation of the dye pair reduces fluorescence quenching, with a change in a fluorescence parameter such as intensity serving as an indication of target amplification.

The change in fluorescence resulting from unfolding or linearizing of the detector oligonucleotides may be detected at a selected endpoint in the reaction. However, because linearized secondary structures are produced concurrently with hybridization or primer extension, the change in fluorescence may also be monitored as the reaction is occurring, i.e., in "real-time". This homogeneous, real-time assay format may be used to provide semiquantitative or quantitative information about the initial amount of target present. For example, the rate at which fluorescence intensity changes during the unfolding or linearizing reaction (either as part of target amplification or in non-amplification detection methods) is an indication of initial target levels. As a result, when more initial copies of the target sequence are present, donor fluorescence more rapidly reaches a selected threshold value (i.e., shorter time to positivity). The decrease in acceptor fluorescence similarly exhibits a shorter time to positivity, detected as the time required to reach a selected minimum value. In addition, the rate of change in fluorescence parameters during the course of the reaction is more rapid in samples containing higher initial amounts of target than in samples containing lower initial amounts of target (i.e., increased slope of the fluorescence curve). These or other measurements as is known in the art may be made as an indication of the presence of target or as an indication of target amplification. The initial amount of target is typically determined by comparison of the experimental results to results for known amounts of target.

Assays for the presence of a selected target sequence according to the methods of the invention may be performed in solution or on a solid phase. Real-time or endpoint homogeneous assays in which the detector oligonucleotide functions as a primer are typically performed in solution. Hybridization assays using the detector oligonucleotides of the invention may also be performed in solution (e.g., as homogeneous real-time assays) but are also particularly well-suited to solid phase assays for real-time or endpoint detection of target. In a solid phase assay, detector oligonucleotides may be immobilized on the solid phase (e.g., beads, membranes or the reaction vessel) via internal or terminal labels using methods known in the art. For example, a biotin-labeled detector oligonucleotide may be immobilized on an avidin-modified solid phase where it will produce a change in fluorescence when exposed to the target under appropriate hybridization conditions. Capture of the target in this manner facilitates separation of the target from the sample and allows removal of substances in the sample which may interfere with detection of the signal or other aspects of the assay.

The following Examples illustrate specific embodiments of the invention described herein. As would be apparent to skilled artisans, various changes and modifications are possible, and are contemplated within the scope of the invention described.

EXAMPLE 1

Assay of Primer Combinations for Robustness

All four primer combinations were tested against a matrix of conditions to determine which of the combinations worked best across the most conditions. The reaction conditions which were varied were as follows:

| Amplification temperature | 52° and 54° C. |
|---|---|
| Potassium phosphate, pH 7.6 | 35 and 45 mM |
| Magnesium acetate | 5 and 6 mM |
| Dimethyl sulfoxide | 3 and 7% (vol/vol) |
| Glycerol | 3 and 7% (vol/vol) |

The reactions (50 μL) also contained 9 units Bst polymerase, 165 units BsoBI restriction endonuclease, 1200 ng human placental DNA, 0.2 mM dATP and dGTP, 1.4 mM $dC_sTP$, 0.5 mM dUTP, 0.1 mg/mL acetylated bovine serum albumin, 1.8% trehalose, 0.36 mM dithiothreitol (DTT) and $1 \times 10^6$ copies of target plasmid DNA. The target plasmid was plasmid pCT16 which contains regions B and F of the Cryptic plasmid (from Serovar J) inserted into pUC 18.

Samples were prepared to contain phosphate, DMSO, glycerol, human DNA and target DNA in a volume of 30 μL. The samples were heat denatured for 2 minutes in a boiling water bath, briefly centrifuged, and placed in a 45° C. Thermal-Lok Dry Bath (U.S.A. Scientific, Fla.). After 2–5 minutes of equilibration, the following components were added in a volume of 10 μL: potassium phosphate, primers, bumpers, dGTP, dATP, $dC_sTP$, BSA, DTT, trehalose, magnesium and 1 unit of uracil-N-DNA glycosylase (UDG). Samples were incubated for 30 minutes. The samples were then transferred to a Thermal-Lok dry bath set to the desired amplification temperature. The following reagents were added in a volume of 10 μL: potassium phosphate, dUTP, BSA, DTT, trehalose, magnesium, Bst, BsoBI and uracil-N DNA glycosylase inhibitor (UDI). Thermal SDA occurred over the next thirty minutes. Reactions were stopped by boiling samples for 5 minutes. Amplified products were detected by the extension of $^{32}$P-labeled probe CTpB4.D1 (SEQ ID NO: 15) hybridized specifically to the central region of the amplicon. Detected samples were run on an 8% polyacrylamide gel and visualized by phosphorimage or by overnight exposure to autoradiographic film.

FIGS. 2A–D show the phosphorimages of the matrix of test conditions. The primer combination is indicated at the bottom of each lane. Under certain conditions only some of the primer combinations will work, while other conditions are favorable for any of the four combinations. Though combinations 1 and 2 appear to work better under a number of conditions, it is not clearly evident that one combination is superior to all others.

Figure 3A:
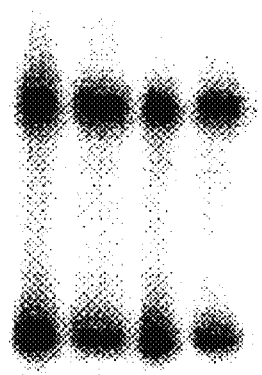
FIGS. 3A and 3B show the phosphorimages of tSDA reactions performed using pCT16 as the target but using two different, but complementary, detectors. The reactions were performed using 3% DMSO, 7% glycerol, 6 mM magnesium, 35 mM potassium phosphate and were amplified at 52° C. The four combinations of primers (1, 2, 3 and 4) were used. The four samples in FIG. 3A were detected with an extension primer which hybridized to the anti-sense strand of the amplified product in FIG. 3B. The same four samples were detected with the complement of the detector used in FIG. 3A. The detector used for the experiments shown in FIG. 3B hybridizes to the sense strand of the amplified product.
Figure 3B:
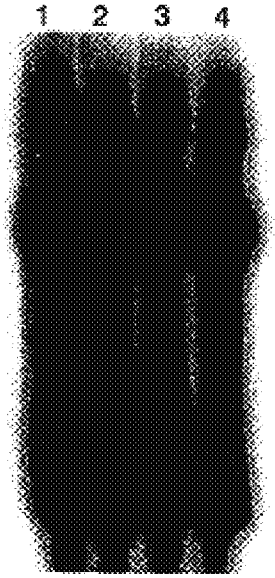

In the same experiment, four of the samples (52° C., 35 mM $KPO_4$, 5 mM MgOAC, 3%DMSO, 7% Glycerol) were detected with a complementary detector, CTpB4.D2 (SEQ ID NO: 16). The results are shown in FIG. 3. The detector which hybridized to the sense strand gave a 50-fold increase in intensity of the phosphorimage which indicates that better sensitivity is achieved with this detector as compared to its complement. Thus, all subsequent examples with System B used detector CTpB4.D2 (SEQ ID NO: 16).

EXAMPLE 2

Assay for Conditions Giving Greatest Sensitivity

In order to select a primer combination and buffer conditions with the greatest sensitivity, each of the above 4 primer combinations was tested at the two best conditions seen in Example 1. These two sets of conditions are as follow:

Condition 1

35 mM potassium phosphate, pH 7.6

6 mM magnesium acetate

3% dimethyl sulfoxide

3% glycerol

Amplification at 54° C.

Condition 2

35 mM potassium phosphate, pH 7.6

6 mM magnesium acetate

3% dimethyl sulfoxide

7% glycerol

Amplification at 54° C.

Figure 4B:
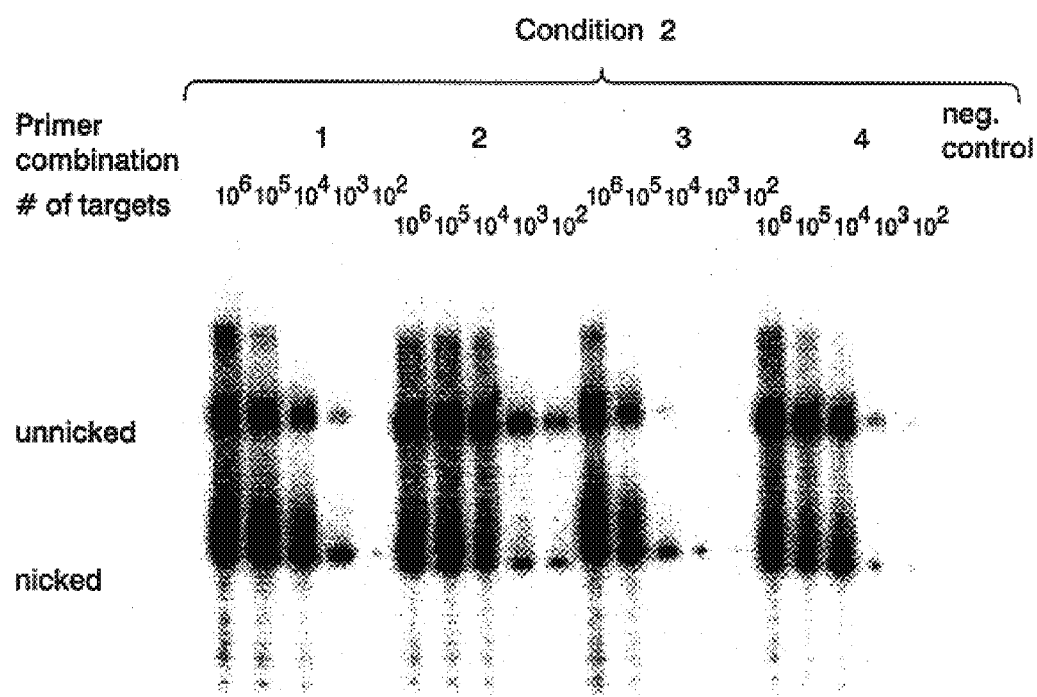
FIG. 4 shows the phophorimage results of performing tSDA using pCT16 as a target and using various combinations of primers and buffer conditions to test sensitivity. Target was present at from $10^2$ to $10^6$ copies. Each of primer combinations 1, 2, 3 and 4 was tested across each range of target copy number. The experiments were performed under two sets of buffer conditions as explained in Example 2.

All other reaction conditions were as described in Example 1. The phosphorimage of the gel is shown in FIG. 4. These results indicate that all combinations of primers worked better under condition 2, and that better sensitivity ($10^2$) was seen with primer combinations 1 and 2 under both conditions. Primer combination 2 was selected for further study. Thus, all subsequent examples for System B use primer combination 2 (CTpB4.S1.1 (SEQ ID NO: 10) and $CTpB4.S_2$ (SEQ ID NO: 12)).

EXAMPLE 3

Assay of the Specificity and Crossreactivity of System B

Figure 5:
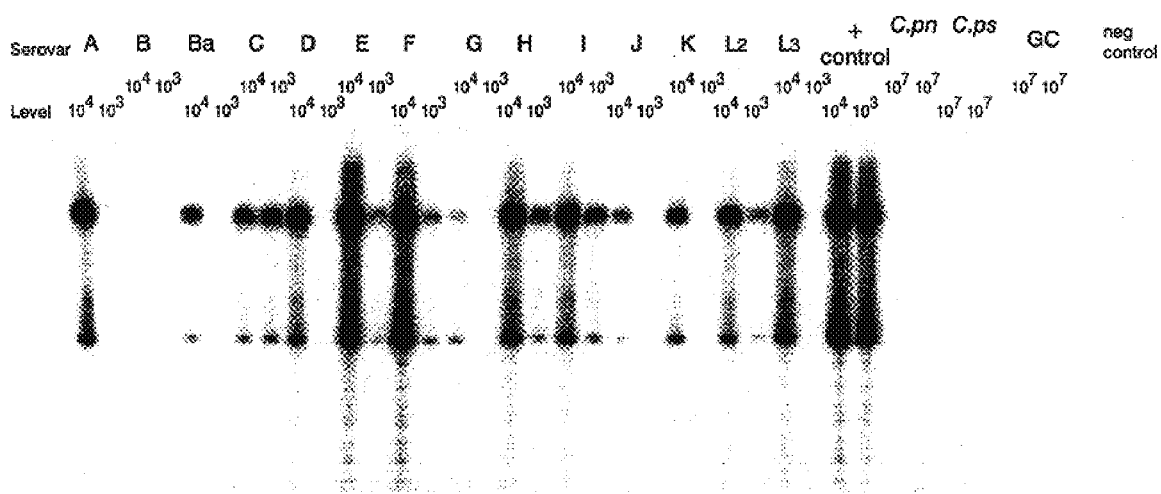
FIG. 5 shows the results of an assay to check the specificity and crossreactivity of primer combination 2. Target nucleic acid consisted of fourteen serovars of C. trachomatis (A, B, Ba, C, D, E, F, G, H, I, J, K L2 and L3) to test specificity as well as C. pneumoniae, C. psittaci and N. gonorrhoeae to test crossreactivity. Each serovar was tested at both $10^4$ and $10^3$ genome copies while the crossreactant tests used $10^7$ genome copies of the tested organisms. Lanes with control (pCT 16) and no target were also included.

An assay was performed to test the ability of primer system B to amplify the multiple serovars of *C. trachomatis*. Fourteen serovars were tested using condition 2 described in Example 2. Each serovar was tested at $10^4$ and $10^3$ genome copies (the actual number of cryptic plasmid copies present in the sample is unknown). Thirteen of the fourteen serovars amplified at the $10^4$ level, and 7 of the fourteen amplified at the $10^3$ level (see FIG. 5). Serovar B did not amplify. Serovar B is 100% identical to the primers and bumpers and it is believed that the lack of amplification was due to an impure sample or low copy number of the plasmid. Two other species of Chlamydia and one strain of *Neisseria gonorrhoeae* were tested at an input level of $10^7$ genome copies. None of these produced a specific amplified product.

EXAMPLE 4

Assay of the Sensitivity in the Presence of Human DNA

Figure 6:
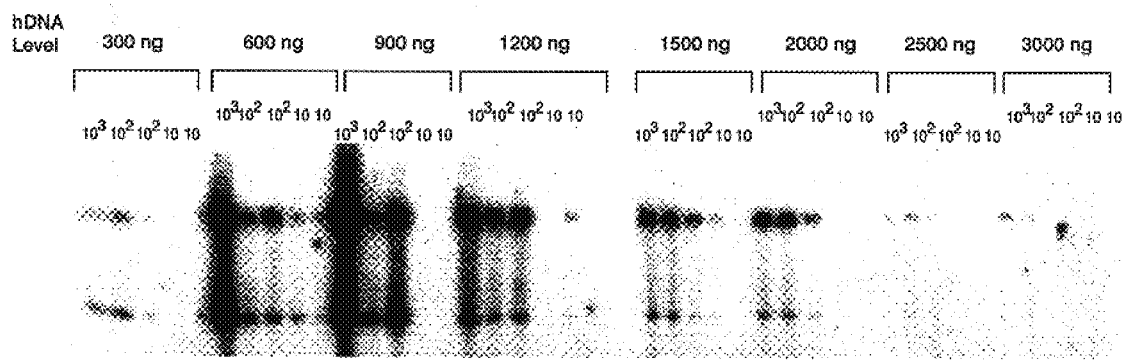
FIG. 6 shows the results of an assay to test the sensitivity of primer combination 2 for C. trachomatis cryptic plasmid in the presence of various amounts of human DNA ranging from 300 to 3000 ng.

An assay was performed to test the system sensitivity in the presence of human DNA, using Condition 2 as described in Example 2 above. Target plasmid was titrated down to 10 copies in the presence of human DNA ranging from 300 to 3000 ng. The results are shown in FIG. 6. Reactions contained $10^3$, $10^2$ (duplicates), and 10 (duplicates) copies of target plasmid DNA for each level of hDNA. A negative control (no target plasmid) was also run at the 1200 ng hDNA level. The system showed 10 copy sensitivity from 600 to 2500 ng of human DNA and $10^2$ sensitivity at 300 and 3000 ng of human DNA.

EXAMPLE 5

Assay for Crossreactivity with Other Microorganisms

Figure 7:
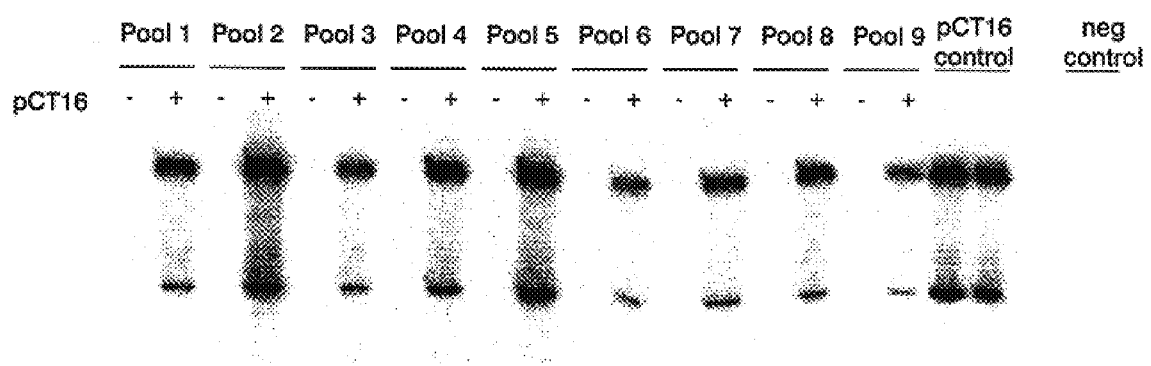
FIG. 7 shows the results of an assay for crossreactivity using primer combination 2. Nine pools consisting of a total of 35 different organisms representing 30 different species were tested to determine if there was any crossreaction. Each species was tested at $10^7$ genomic copies. For each pool, the left lane indicates amplification of the pool alone, whereas the right lane indicates the amplification of the pool plus 200 copies of pCT 16.

An assay was performed to test whether there would be crossreactivity with potential genitourinary contaminants. Condition 2 as outlined in Example 2 was used. A total of thirty-five organisms sampling thirty species were tested. These organisms are listed in Table 1. Nine pools were prepared to each contain three or four species of DNA at $10^7$ genome copies per species. Each pool was amplified in the absence of target plasmid or in the presence of 200 copies of plasmid pCT16. The pools with added target served as amplification controls. None of the pools without added target showed amplification while all the pools with added plasmid target amplified specific product. These results are shown in FIG. 7.

TABLE 1

| Pool | Organism | Strain |
|---|---|---|
| 1 | Neisseria gonorrhoeae | ATCC 19424 |
|   | Neisseria gonorrhoeae | ATCC 35541 |
|   | Neisseria gonorrhoeae | BDMS 2900 |
|   | Neisseria gonorrhoeae | BDMS 1632 |
| 2 | Neisseria lactamica | ATCC 23970 |
|   | Neisseria lactamica | ATCC 23972 |
|   | Neisseria meningitidis | ATCC 13090 |
|   | Neisseria meningitidis | ATCC 13077 |
| 3 | Staphylococcus aureus | ATCC 12598 |
|   | Streptococcus faecalis | ATCC 29212 |
|   | Group A strep | ATCC 16915 |
|   | Group B strep | ATCC 12386 |
| 4 | Salmonella typhimurium | ATCC 13311 |
|   | Salmonella minnesota | ATCC 9700 |
|   | Escherichia coli | ATCC 11775 |
|   | Klebsiella pneumoniae | ATCC 13883 |
| 5 | Proteus mirabilis | ATCC 29906 |
|   | Moraxella lacunata | ATCC 17967 |
|   | Haemophilus influenzae | ATCC 33533 |
|   | Acinetobacter lwoffii | ATCC 19001 |
| 6 | Gardenerella vaginalis | ATCC 14018 |
|   | Mycoplasma orale | ATCC 73714 |
|   | Trichomonas vaginalis | ATCC 30001 |

TABLE 1-continued

| Pool | Organism | Strain |
|---|---|---|
|   | Candida albicans | ATCC 44808 |
| 7 | Herpes Simplex Virus-1 HSV-1 | McIntyre |
|   | Herpes Simplex Virus-2 HSV-2 | G |
|   | Peptostreptococcus productus | ATCC 27340 |
| 8 | Neisseria flavescens | ATCC 13120 |
|   | Neisseria sicca | ATCC 29193 |
|   | Neisseria cinerae | ATCC 14685 |
|   | Neisseria elongata | ATCC 25295 |
| 9 | Neisseria mucosa | ATCC 19696 |
|   | Neisseria subflava | ATCC 14799 |
|   | Branhamella catarrhalis | ATCC 25240 |
|   | Kingella kingae | ATCC 23330 |

EXAMPLE 6

Primers, Bumpers and Detectors from Cryptic Plasmid Region F for Performing tSDA Sequence data of the F region of the Cryptic plasmid from four human serovars of *C. trachomatis* was available from the Genbank database. Four other serovars were sequenced in this region. A composite alignment was used to design tSDA primer sets to overcome sequence variations. The primers, bumpers and detectors chosen to be used with Region F are set out below. BsoBI sites within the tSDA primers are italicized and the hybridization region is underlined. Detector probes D1L and D2L were used in radiolabel extension assays, D3L and D4L were used in capture/detector assays, and FD1 was used as a fluorescent labeled detector.

Bumpers

CtpF8.BL 5'-CAGCAAATAATCCTTGG-3' (SEQ ID NO: 18)

CtpF8.BR 5'-CATTGGTTGATGAATTATT-3' (SEQ ID NO: 19)

tSDA Primers

CtpF8.AL1
5'-CGATTCCGCTCCAGACTTCTCGGGACAAA ATCAACACCTG-3' (SEQ ID NO: 20)

CtpF8.AL2
5'-CGATTCCGCTCCAGACTTCTCGGGACAAA ATCAACACCTGT-3' (SEQ ID NO: 21)

CtpF8.AR1
5'-ACCGCATCGAATGCATGTCTCGGGGAGACT GTTAAAGATA-3' (SEQ ID NO: 22)

CtpF8.AR2
5'-ACCGCATCGAATGCATGTCTCGGGGAGACT GTTAAAGATAT-3' (SEQ ID NO: 23)

CtpF8.AR3
5'-ACCGCATCGAATGCATGTCTCGGGGAGACT GTTAAAGATATT-3' (SEQ ID NO: 24)

32P Detectors

CtpF8.D1L 5'-GTCGCAGCCAAAATG-3' (SEQ ID NO: 25)

CtpF8.D2L 5'-ACAGCTTCTGATGGAA-3' (SEQ ID NO: 26)

Chemiluminescent Capture/Detector Probes

CtpF8.D3L 5'-GTCGCAGCCAAAAT-(alkaline phosphatase×3)-3' (SEQ ID NO: 27)

CtpF8.D4L 5'-(biotinx3)-GACAGCTTCTGATGGAA-3' (SEQ ID NO: 28)

Homogenous (Fluorescent) Detector Probe

CtpF8.FD1   5'-TAGCACCCGAGTGCTCGCAGCCAAAATGACAGCTTCTGATGGAA-3'   (SEQ ID NO: 29)

EXAMPLE 7

Primer Screen for Region F

Primers of different lengths (and consequently different Tm) were screened in an experiment varying temperature (50° C. or 52° C.), potassium phosphate (25 mM or 35 mM), glycerol (3.5% or 7%), DMSO (3% or 8%) and human placental DNA (300 ng or 1200 ng). Other components for the tSDA reactions were: 6 mM magnesium acetate, 160 units BsoBI, 9 units Bst polymerase, 0.2 mM dATP, 1.4 mM $d_sCTP$, 0.2 mM dGTP, 0.5 mM dUTP, 0.5 μM each primer, 0.05 μM each bumper, 1 unit UDG, 5 units UDI, 100 μg/mL BSA, 0.36 mM DTT, 1.86% trehalose. The target was $10^6$ genomes of C. trachomatis LGVII. Decontamination was at 45° C. for 30 minutes and amplification was at either 50° C. or 52° C. for 30 minutes.

All primer combinations (6) were tested. Amplified products were detected in an extension reaction using the radiolabelled detector probe CtpF8.D1L (SEQ ID NO: 20). After separation of amplified products on an 8% acrylamide gel, quantification of intensity of radiolabeled products was performed with a Molecular Dynamics 445SI Phospholmager and ImageQuant v1.1 software.

All primer combinations produced detectable amplification products under at least five of the eight conditions tested and listed below.

extension reaction and quantified using ImageQuant v1.1 software. The results are shown in Table 2. Any intensity below 2×background is reported as zero. The data demonstrate that the tSDA primer set F can detect 10 copies (3/3 replicates) and can detect 1 copy (1/3 replicates) of the target region.

TABLE 2

| Copies of pCT16 | Intensity | Genome Copies of Serovar LGV II | Intensity (pixels) |
|---|---|---|---|
| $10^6$ | 54,336,500 | $10^6$ | 64,616,550 |
| $10^5$ | 62,185,822 | $10^5$ | 76,821,582 |
| $10^4$ | 61,722,424 | $10^4$ | 57,716,379 |
| $10^3$ | 44,104,645 | $10^3$ | 14,191,912 |
| $10^3$ | 37,944,957 | | |
| $10^2$ | 6,427,450 | $10^2$ | 1,534,883 |
| $10^2$ | 14,184,075 | | |
| $10^2$ | 9,067,676 | | |
| 10 | 2,004,088 | 10 | 32,110 |
| 10 | 717,772 | | |
| 10 | 2,178,641 | | |
| 1 | 101,144 | 1 | 31,291 |
| 1 | 0 | | |
| 1 | 0 | | |
| 0 | 0 | | |

|  | 1 | 2 | 3 | 4 | 5 | 6 | 7 | 8 |
|---|---|---|---|---|---|---|---|---|
| Temp | 50° | 50° | 50° | 50° | 52° | 52° | 52° | 52° |
| Phosphate | 25 mM | 25 mM | 35 mM | 35 mM | 25 mM | 25 mM | 35 mM | 35 mM |
| Glycerol | 3.5% | 7% | 3.5% | 7% | 3.5% | 7% | 3.5% | 7% |
| DMSO | 3% | 8% | 8% | 3% | 8% | 3% | 3% | 8% |
| hpDNA | 1200 ng | 300 ng | 300 ng | 1200 ng | 1200 ng | 300 ng | 300 ng | 1200 ng |

One primer combination, AL1/AR1, produced strong amplification in six of the conditions tested. The best amplification was observed when using 35 mM potassium phosphate, 3% DMSO, 7% glycerol, 1200 ng human DNA and 50° C. amplification. This primer combination, along with the bumpers, make up primer set F.

EXAMPLE 8

Sensitivity Titration for Primer Set F

A titration of a plasmid, pCT16, constructed to contain one copy of the target region from Chlamydia trachomatis serovar J, was tested from $10^6$ copies down to 1 copy. Also, a titration of a genomic DNA preparation from C. trachomatis elementary bodies was carried out for comparison. The conditions used for the tSDA were the same as those described in Example 7: 35 mM potassium phosphate, 3% DMSO, 7% glycerol, 6 mM magnesium acetate, 1200 ng human placental DNA and a 50° C. amplification temperature. After amplification, products were detected using CtpF8.D1L (SEQ ID NO: 25) in a radiolabelled probe

EXAMPLE 9

Specificity of Primer Set F for C. trachomatis Serovars

To determine whether system F could amplify all of the C. trachomatis serovars, whole genomic DNA preparations from thirteen serovars were tested. Serovar LGV I was not available for testing. These were tested under the same amplification conditions as in Example 8 and using $10^3$ genomes. Each assay was performed in duplicate. The results are shown in Table 3. Any intensity less than 2×above the background level was reported as zero.

TABLE 3

| Serovar | Intensity (pixels) | Intensity (pixels) |
|---|---|---|
| A | 218,413 | 56,556 |
| B | 0 | 0 |
| Ba | 187,056 | 122,053 |
| C | 178,899 | 126,053 |

TABLE 3-continued

| Serovar | Intensity (pixels) | Intensity (pixels) |
|---|---|---|
| D | 51,968 | 205,425 |
| E | 256,928 | 715,980 |
| F | 309,899 | 402,525 |
| G | 0 | 53,155 |
| H | 465,217 | 553,424 |
| I | 265,694 | 446,492 |
| J | 250,981 | 281,921 |
| K | 60,013 | 148,717 |
| LIII | 220,077 | 119,152 |
| Negative | 0 | 0 |

The data in Table 3 along with the data in Example 8 demonstrate that primer set F can detect at least 13 of the 15 serovars of C. trachomatis at $10^3$ genomes. Only 14 of the 15 were tested because serovar LGV I was unavailable. The one serovar which gave a negative result is Serovar B. Serovar B genomic DNA was not detected by any of the amplification systems specific for C. trachomatis (see the above Examples), suggesting that the serovar B DNA preparation is suspect.

EXAMPLE 10

Further Specificity Testing of Primer Sets B and F for C. trachomatis Serovars

Because of the susceptibility of serovar B DNA and the unavailability of serovar LGV 1 DNA as reported in Example 9 above, the same conditions of Example 9 were used with only these two serovar DNAs to determine whether systems B and F could also amplify C. trachomatis serovars B and LGV 1. Each assay was performed in duplicate for $10^3$ and $10^4$ genomes. The results are shown in Table 4. Any intensity less than 2×above the background level was reported as zero.

TABLE 4

| Serovar | # of Genomes | System F | System B |
|---|---|---|---|
| B | $10^4$ | 14,592 | 71 |
| B | $10^4$ | 8,072 | 1,286 |
| B | $10^3$ | 9,859 | 0 |
| B | $10^3$ | 134 | 52 |
| LGV 1 | $10^4$ | 8,888 | 8,260 |
| LGV 1 | $10^4$ | 15,663 | 5,371 |
| LGV 1 | $10^3$ | 1,032 | 140 |
| LGV 1 | $10^3$ | 6,728 | 0 |

Thus, it was concluded that System F could amplify and detect both serovar B and serovar LGV 1 at $10^3$ genomes, and that System B could amplify and detect serovar B at $10^4$ genomes and serovar LGV 1 at $10^3$ genomes.

EXAMPLE 11

Optimization of Reaction Conditions for Primer Set F

Primer set F was used in a series of assays utilizing a variety of reaction conditions. The assays used a target level of 100 copies of pCT16. Amplification was seen under all of the following reaction condition ranges:

| | |
|---|---|
| Amplification temperature | 50–54° C. |
| Potassium phosphate | 25–35 mM |
| DMSO | 3–7% (vol/vol) |
| Glycerol | 3–7% (vol/vol) |
| Magnesium acetate | 5–6 mM |
| Human placental DNA | 300–3050 ng |

In several instances the above ranges were the limits of what was tested and it is likely that amplification will occur with reaction conditions beyond the ranges shown above. The conditions identified as producing the greatest amplification were:

| | |
|---|---|
| Amplification temperature | 52° C. |
| Potassium phosphate | 35 mM |
| DMSO | 7% (vol/vol) |
| Glycerol | 7% (vol/vol) |
| Magnesium acetate | 5 mM |
| Human placental DNA | 1200 ng |

EXAMPLE 12

Assay of Crossreactivity of Primer Set F

There are potential cross-reactant bacteria and viruses commonly found in genitourinary clinical specimens. Thermal SDA reactions were performed using primer set F using the best assay conditions of Example 11. The potential cross-reactant specimens were tested at $10^7$ genomes. These were tested in pooled samples of four species, with a control of the same pool spiked with 100 copies of pCT16 to show that no inhibition of amplification occurred. The results are shown in Table 5. None of the cross-reactants was amplified or detected by primer set F.

TABLE 5

| Organism | Strain | Result | Organism | Strain | Result |
|---|---|---|---|---|---|
| Chlamydia psittaci | TWAR | — | Branhamella catarrhalis | ATCC 25240 | — |
| Chlamydia pneumoniae | Borg | — | Moraxella lacunata | ATCC 17967 | — |
| Neisseria gonorrhoeae | BDMS 1632 | — | Kingella kingae | ATCC 23330 | — |
| Neisseria gonorrhoeae | ATCC 19424 | — | Salmonella typhimurium | ATCC 13311 | — |
| Neisseria gonorrhoeae | BDMS 2900 | — | Salmonella minnesota | ATCC 9700 | — |
| Neisseria gonorrhoeae | ATCC 35541 | — | Staph. aureus | ATCC 12598 | — |
| Neisseria meningitidis | ATCC 13090 | — | Acinetobacter lwoffi | ATCC 19001 | — |
| Neisseria meningitidis | ATCC 13077 | — | E. coli | ATCC 11775 | — |
| Neisseria lactamica | ATCC 23970 | — | Klebsiella pneumoniae | ATCC 13883 | — |

TABLE 5-continued

| Organism | Strain | Result | Organism | Strain | Result |
|---|---|---|---|---|---|
| Neisseria lactamica | ATCC 23972 | — | Gardnerella vaginalis | ATCC 14018 | — |
| Neisseria flavescens | ATCC 13120 | — | Streptococcus Group A | ATCC 16915 | — |
| Neisseria sicca | ATCC 29193 | — | Streptococcus Group B | ATCC 12386 | — |
| Neisseria subflava | ATCC 14799 | — | Proteus mirabilis | ATCC 29906 | — |
| Neisseria cinerea | ATCC 14685 | — | Haemophilus influenzae | ATCC 33533 | — |
| Neisseria elongata | ATCC 25295 | — | Mycoplasma orale | ATCC 23714 | — |
| Neisseria mucosa | ATCC 19696 | — | Herpes simplex V-1 | McINTYRE | — |
| Streptococcus faecalis | ATCC 27340 | — | Herpes simpiex V-2 | Strain G | — |
| Candida albicans | ATCC 44808 | — | Trichomonas vaginalis | ATCC 30001 | — |
| Peptostreptococcus productus | ATCC 27340 | — | | | |

EXAMPLE 13

Homogeneous Real Time Fluorescent tSDA

Detection of C. trachomatis in Systems B and F

The primer sets F and B were also useful in performing homogeneous real time fluorescent tSDA reactions. Such reactions use a detector which includes a hairpin sequence and an acceptor and a donor fluorescent molecules. One such detector which works well for use with the system F primer set is CTpF8.FD1 5'-TAGCACCCGAGTGCTCGCAGCCAAA ATGACAGCTTCTGATGGAA-3' (SEQ ID NO: 29). A detector which works well for use with system B is CTpB4.FD1 5'-TAGCACCCGAGTGCTTTGACGATTTTCTCCAAC CGA TGAGTTGAT-3' (SEQ ID NO: 17). The first 15 bases of these sequences include a hairpin structure as well as a BsoBI restriction site. Bases 2–6 can base pair with bases 15–11. Furthermore, base 1 is modified by addition of FAM and base 15 is modified by addition of ROX. This hairpin structure (the first 15 bases of SEQ ID NO: 29) is 5'-(FAM) *TAGCACCCGAGTGCT*(ROX)-3' (SEQ ID NO: 30). Bases 6–11 are shown in italics and represent the BsoBI restriction site.

The protocol for performing homogeneous real time fluorescent tSDA is similar to that for regular tSDA. One such protocol, which has been adapted for larger volume reactions for use with microtiter well formats, but which follows the tSDA protocol in ratios of components is as follows:

1. Equilibrate a Thermal-Lok bath to 45° C. and equilibrate another Thermal-Lok bath to 52° C. using an Electro-Therm digital thermometer after filling wells with 1 mL of water. Also equilibrate a dry Thermal-Lok bath to 54° C.
2. Prepare the tSDA reaction buffer and prepare the decontamination mix. Keep these at room temperature.
3. Add 65 μL of tSDA reaction buffer to each 0.5 mL Eppendorf Safelok tube.
4. Add 5 μL of template diluted in 10 ng/μL human DNA per tube.
5. Place tubes in boiling waterbath for 2 minutes.
6. Transfer tubes to microfuge and pulse spin.
7. Transfer tubes to the 45° C. Thermal-Lok for 5 minutes.
8. Add 15 μL of decontamination mix to each tube, vortex briefly, and incubate for 20 minutes.
9. Prepare amplification mix and store at room temperature.
10. Place microtiter wells in metal tray and place on top of 54° C. Thermal-Lok to preheat.
11. Transfer tubes to 52° C. Thermal-Lok for 5 minutes.
12. Transfer 85 μL of the reaction into appropriate microtiter well. For end point reactions only, leave sample in tube.
13. Add 15 μL of amplification mix to each well. Seal wells with a self adhesive acetate sheet. For end point reactions, add 15 μl of amplification mix to each tube, vortex and continue incubating in thermal-lok for 60 minutes.
14. Place the tray into a fluorescent plate reader at 52° C. and collect RFU data over 60 minutes. For end point reactions, transfer contents of tubes to microtiter wells and take a single reading for each well.

EXAMPLE 14

Sensitivity of Systems B and F Using Homogeneous Detection

To test the sensitivity of using primer systems F and B with the CtpF8.FD1 and CTpB4.FD1 detectors in a homogeneous real time fluorescent tSDA reaction, a series of such reactions was performed using plasmid pCT16 as the target at different copy numbers. For System B, the end point protocol described in Example 12 was used. The final reaction conditions were: 35 mM potassium phosphate 3% DMSO, 7% glycerol, 6 mM magnesium acetate, 40 units Bst, 640 units BsoBI, 2400 ng human placental DNA, 0.2 mM dATP and dGTP, 1.4 mM dCsTP, 0.5 mM dUTP, 0.1 mg/ml acetylated bovine serum albumin, 1.8% trehalose, 0.36 mM DTT, and 200 mM CTpB4.FD1 (SEQ ID NO: 17). Amplification was done at 54° C. and decontamination enzyme (UDG) and inhibitor (UDI) was used. The following results were obtained by reading the samples after 60 minutes incubation (excitation 485 nm, emission 538 nm):

| Plasmid Copy | End Point RFU | Endpoint RFU/ Mean Background |
|---|---|---|
| 500 | 2.52 | 4.8 |
|  | 7.27 | 14.0 |
|  | 14.35 | 27.6 |
| 200 | 6.72 | 12.9 |
|  | 2.14 | 4.1 |
|  | 11.64 | 22.4 |
| 50 | 1.20 | 2.3 |
|  | 0.66 | 1.3 |
|  | 0.43 | 0.8 |

-continued

| Plasmid Copy | End Point RFU | Endpoint RFU/ Mean Background |
|---|---|---|
| 0, Background | 0.57 | |
| | 0.51 | |
| | 0.48 | |

The results indicate a sensitivity of 50 copies of pCT16 for one out of three replicates, when positive is defined as 2×above mean background.

For system F, decontamination and amplification mixes were prepared as previously described in Example 12 but at a 10×concentration level for all reagents. Fifteen microliters of decontamination mix or ten microliters of amplification mix were spotted into the bottoms of microtiter wells and dried in a low humidity drying chamber. Decontamination wells and amplification wells were packaged separately with desiccant until use.

Wells containing decontamination spots were prewarmed at 45° C. on a Thermal-Lok heat block for five minutes. Samples containing purified water, potassium phosphate, glycerol, DMSO, human placental DNA, and plasmid pCT16 were boiled for two minutes and spun quickly in a microcentrifuge to pool. One hundred fifty microliters of each sample were pipetted into the prewarmed decontamination wells, sealed with adhesive film and incubated for twenty minutes at 45° C. The wells were moved to a second Thermal-Lok heat block set to achieve a temperature of 52° C. in the wells. Coincidentally, an equivalent number of the above described spotted amplification wells were placed on the same heat block to prewarm. After five to ten minutes, the film was removed from the decontamination wells, and one hundred microliters of sample was removed from each well and pipetted into an amplification well (one amplification well per sample). The final reaction conditions in the micro wells after the rehydration of the amplification spot were: 35 mM potassium phosphate, 7% glycerol, 7% DMSO, 5 mM magnesium acetate, 0.2 mg/mL acetylated BSA, 1.86% trehalose, 0.36 mM dithiothreitol, 0.7 mM α-thiolated dCTP, 0.25 mM dUTP, 0.1 mM dATP, 0.1 mM dGTP, 40 units Bst polymerase, 640 units BsoBI, 1 unit Uracil DNA glycosylase, 5 units uracil DNA glycosylase inhibitor, 0.5 µM AR1 (primer), 0.3 µM AL1 (primer), 0.05 µM BL1 and BR1 (bumpers), 0.2 µM FD1 (detector oligo) and 2400 ng human placental DNA. Amplification wells were sealed using a fresh sheet of adhesive film, and immediately transferred to a PerSeptives plate reader which had been set to maintain a constant incubation temperature of 52° C. Wells were read immediately and at one minute intervals for the following sixty minutes. The samples were excited at 485 nm and the emitted fluorescence was monitored at 530 nm. Table 6 shows the results. These results indicate a system sensitivity of 10 copies of target DNA.

TABLE 6

| Plasmid Copy # | Initial RFU | Final RFU | Difference |
|---|---|---|---|
| 0 | 298 | 334 | 36 |
| 0 | 361 | 407 | 46 |
| 10 | 370 | 726 | 356 |
| 10 | 295 | 299 | 4 |
| 50 | 390 | 718 | 328 |

TABLE 6-continued

| Plasmid Copy # | Initial RFU | Final RFU | Difference |
|---|---|---|---|
| 50 | 357 | 1076 | 719 |
| 100 | 299 | 1164 | 865 |
| 100 | 391 | 1706 | 1315 |

EXAMPLE 15

Sensitivity of System F Using Homogeneous Detection

A second set of experiments was performed to check the sensitivity of system F. Whereas Example 14 used plasmid pCT16 as the target, for this second set of experiments, elementary bodies of C. trachomatis LGV2 were used as the target. Reactions were performed as in Example 13. The final reaction conditions were as described in Example 14 except the following: 1.4 mM thiolated dCTP, 0.5 mM dUTP, 0.2 mM dATP and dGTP. RFU data was collected every minute for the 60 minute amplification time. The difference in RFU between time 0 and time 60 is shown in Table 7 for two replicates at each level. Again, this fluorescent detector based system F can amplify and detect above background level as few as 10 elementary bodies of C. trachomatis.

TABLE 7

| Number of Elementary Bodies | Change in RFU Replicate 1 | Change in RFU Replicate 2 |
|---|---|---|
| 300 | 1142 | 769 |
| 250 | 1430 | 1015 |
| 200 | 836 | 813 |
| 150 | 401 | 307 |
| 100 | 262 | 573 |
| 80 | 717 | 407 |
| 60 | 381 | 424 |
| 40 | 257 | 461 |
| 20 | 468 | 349 |
| 10 | 158 | 66 |
| Positive control pCT16 - 150 copies | 586, 215, 524 | |
| Negative control | 75 | |

EXAMPLE 16

Specificity of System F Using Homogenous Detection

The specificity of the CtpF811.FD1 system as used in homogeneous real time fluorescent tSDA was tested. Reactions were performed as in Example 14. Cross reactant pools were tested at $10^7$ genomes per reaction. Amplifications were performed in a PerSeptive Biosystems CytoFluor 4000 plate reader. RFU data was collected every minute for the 60 minute amplification time. The difference in RFU from time 0 to time 60 is shown in Table 8. None of the pools show amplification or detection of the possible cross-reactants which were tested.

TABLE 8

| Pool Cross-Reactant | Change in RFU |
|---|---|
| 1 Neisseria gonorrhoeae ATCC 19424 Neisseria gonorrhoeae ATCC 35541 | 25 |

TABLE 8-continued

| Pool | Cross-Reactant | Change in RFU |
|---|---|---|
| | Neisseria gonorrhoeae BDMS 2900 | |
| | Neisseria gonorrhoeae BDMS 1632 | |
| 2 | Neisseria meningitidis ATCC 13077 | 24 |
| | Neisseria meningitidis ATCC 13090 | |
| 3 | Staph. aureus ATCC 12598 | 13 |
| | Streptococcus grp A ATCC 16915 | |
| | Streptococcus grp B ATCC 12386 | |
| | Streptococcus faecalis ATCC 29212 | |
| 4 | Salmonella minnesota ATCC 9700 | 20 |
| | Salmonella typhimurium ATCC 13311 | |
| | E. coli ATCC 11775 | |
| | Klebsiella pneumoniae ATCC 13883 | |
| 5 | Proteus mirabilis ATCC 29906 | 13 |
| | Moraxella lacunata ATCC 17967 | |
| | Haemophilus influenzae ATCC 33533 | |
| 6 | Gardenerella vaginalis ATCC 14018 | 28 |
| | Mycoplasma orale ATCC 23714 | |
| | Trichomonas vaginalis ATCC 30001 | |
| | Candida albicans ATCC 44808 | |
| 7 | HSV 1 McIntyre | 13 |
| | HSV 2 G | |
| | Peptostreptococcus productus ATCC 44808 | |
| 8 | Neisseria flavescens ATCC 13120 | −1 |
| | Neisseria sicca ATCC 29193 | |
| | Neisseria cinera ATCC 14685 | |
| | Neisseria elongata ATCC 25295 | |
| 9 | Neisseria mucosa ATCC 19696 | 23 |
| | Neisseria subflava ATCC 14799 | |
| | Branhamella catarrhalis ATCC 25240 | |
| | Kingella kingae ATCC 23330 | |
| 10 | Neisseria meningitidis ATCC 14632 | 0 |
| | Neisseria meningitidis ATCC 13077 | |
| | Neisseria meningitidis ATCC 13102 | |
| | Neisseria meningitidis ATCC 13113 | |
| | Neisseria meningitidis ATCC 35559 | |
| 11 | Neisseria lactamica ATCC 44418 | 15 |
| | Neisseria lactamica ATCC 49142 | |
| | Neisseria lactamica ATCC 23971 | |
| | Neisseria lactamica ATCC 23972 | |
| 12 | Neisseria lactamica ATCC 23970 | 30 |
| 13 | Positive control pCT16 - 100 copies | 401, 150 |
| 14 | Negative control | 22, 27 |

While the invention has been described with some specificity, modifications apparent to those with ordinary skill in the art may be made without departing from the scope of the invention. Various features of the invention are set forth in the following claims.

---

What is claimed is:

1. An isolated polynucleotide consisting of a nucleic acid sequence selected from the group consisting of CTpB4.S1 (SEQ ID NO: 9) and CTpB4.S1.1 (SEQ ID NO: 10).

2. An isolated polynucleotide consisting of a nucleic acid sequence selected from the group consisting of CTpB4.S2 (SEQ ID NO: 12) and CTpB4.S2.1 (SEQ ID No): 13).

3. An isolated polynucleotide consisting of a nucleic acid sequence selected from the group consisting of CTpB4.B1 (SEQ ID NO: 11) and CTpB4.B2 (SEQ ID NO: 14).

4. An isolated polynucleotide consisting of a nucleic acid sequence selected from the group consisting of CTpB4.D1 (SEQ ID NO: 15), a nucleic acid molecule fully complementary to SEQ ID NO: 15, CTpB4.D2 (SEQ ID NO: 16), a nucleic acid molecule fully complementary to SEQ ID NO: 16, CTpB4.FD1 (SEQ ID NO: 17) and a nucleic acid molecule fully complementary to SEQ ID NO: 17.

5. The polynucleotide of claim 4 wherein said polynucleotide comprises a detectable marker.

6. The polycleotide of claim 5 wherein said detectable marker is selected from the set consisting of a radioactive marker and a fluorescence marker.

7. An isolated polynucleotide consisting of a nucleic acid sequence selected from the group consisting of CTpB4.FD1 (SEQ ID NO: 17), CTpF8.FD1 (SEQ ID NO: 29) and SEQ ID NO: 30.

8. The polynucleotide of claim 7 wherein said polynucleotide comprises a fluorescence marker.

9. An isolated polynucleotide consisting of a nucleic acid sequence selected from the group consisting of CTpB1P (SEQ ID NO: 1), CTpB2P (SEQ ID NO: 2), CTpB3N (SEQ ID NO: 3) and CTpB4N (SEQ ID NO: 4).

10. An isolated polynucleotide consisting of a nucleic acid sequence selected from the group consisting of CTpFPL (SEQ ID NO: 5), CTpFPR (SEQ ID NO: 6), CTpFSL (SEQ ID NO: 7) and CTpFSR (SEQ ID NO: 8).

11. A kit comprising:

a) one or more primers selected from the group consisting of CTpB4.S1 (SEQ ID NO: 9) and CTpB4.S1.1 (SEQ ID NO: 10), b) one or more primers selected from the group consisting of CTpB4.S2 (SEQ ID NO: 12) and CTpB4.S2.1 (SEQ ID NO: 13), c) bumpers CTpB4.B1 (SEQ ID NO: 11) and CTpB4.B2 (SEQ ID NO: 14), and d) one or more detectors selected from the group consisting of CTpB4.D1 (SEQ ID NO: 15), a nucleic acid molecule fully complementary to SEQ ID NO: 15, CTpB4.D2 (SEQ ID NO: 16), a nucleic acid molecule fully complementary to SEQ ID NO: 16, CtpB4.FD1 (SEQ ID NO: 17) and a nucleic acid complementary to SEQ ID NO: 17.

12. The kit of claim 11 wherein said one or more detectors comprises a detectable marker.

13. A method for detecting the presence or absence of *Chlamydia trachomatis* in a sample, said method comprising the steps of:

a) treating said sample using a pair of nucleic acid primers in a nucleic acid amplification reaction wherein a first primer is selected from the group consisting of CTpB4.S1 (SEQ ID NO: 9) and CTpB4.S1.1 (SEQ ID NO: 10) and a second primer is selected from the group consisting of CTpB4.S2 (SEQ ID NO: 12) and CTpB4.S2.1 (SEQ ID NO: 13), and b) detecting any amplified nucleic acid product, wherein detection of amplified product indicates presence of *Chlamydia trachomatis*.

14. The method of claim 13 wherein said nucleic acid amplification reaction is a Strand Displacement Amplification (SDA) reaction.

15. The method of claim 14 wherein said SDA reaction utilizes CTpB4.B1 (SEQ ID NO: 11) and CTpB4.B2 (SEQ ID NO: 14) as bumpers.

16. The method of claim 13 wherein detecting said amplified nucleic acid product is conducted by hybridizing said amplified nucleic acid product with a detector selected from the group consisting of CTpB4.D1 (SEQ ID NO: 15), a nucleic acid molecule fully complementary to SEQ ID NO: 15, CTpB4.D2 (SEQ ID NO: 16), a nucleic acid molecule fully complementary to SEQ ID NO: 16, CtpB4.FD1 (SEQ ID NO: 17) and a nucleic acid molecule fully complementary to SEQ ID NO: 17.

17. The method of claim 14 wherein said SDA reaction is a thermophilic Strand Displacement Amplification (tSDA) reaction.

18. The method of claim 17 wherein said tSDA reaction is a homogeneous fluorescent real time tSDA reaction.

19. The method of claim 18 wherein said homogeneous fluorescent real time tSDA reaction utilizes CTpB4.B1 (SEQ ID NO: 11) and CTpB4.B2 (SEQ ID NO: 14) as bumpers.

20. The method of claim 19 wherein said first primer is CTpB4.S1.1 (SEQ ID NO: 10) and said second primer is CTpB4.S2 (SEQ ID NO: 12).

21. The method of claim 20 wherein detecting said amplified nucleic acid product is conducted by hybridizing said amplified nucleic acid product with detector CtpB4.FD1 (SEQ ID NO: 17).

* * * * *